United States Patent [19]

McCarthy et al.

[11] Patent Number: 4,659,658

[45] Date of Patent: Apr. 21, 1987

[54] LECTIN-COATED LATEX AGGLUTINATION ASSAY FOR NEISSERIA GONORRHOEAE

[75] Inventors: Laurence R. McCarthy; H. Mark Perks, both of Baltimore, Md.

[73] Assignee: Becton, Dickinson and Company, Franklin Lakes, N.J.

[21] Appl. No.: 686,190

[22] Filed: Dec. 26, 1984

[51] Int. Cl.$^4$ ............... G01N 33/546; G01N 33/569; G01N 33/571

[52] U.S. Cl. ................................ 435/34; 435/7; 435/29; 435/810; 435/871; 436/511; 436/534; 436/808; 436/827

[58] Field of Search ............... 436/511, 523, 533, 534, 436/827, 808; 435/4, 29, 34, 7

[56] References Cited

U.S. PATENT DOCUMENTS

| | | | |
|---|---|---|---|
| 4,105,598 | 8/1978 | Yen | 435/34 |
| 4,298,689 | 11/1981 | Doyle | 436/827 X |
| 4,308,026 | 12/1981 | Mochida | 436/523 X |
| 4,493,793 | 1/1985 | Chu | 436/827 X |
| 4,508,829 | 4/1985 | Sulitzeanu | 436/827 X |

OTHER PUBLICATIONS

Yajko, D. M. et al., J. Clin. Microbiol., 19(3), 380-382 (1984).
Doyle, R. J. et al., J. Clin. Microbiol., 19(3), 383-387 (1984).
Slifkin, M. et al., J. Clin. Microbiol., 19(1), 83-84 (1984).
D'Amato, R. F. et al., J. Clin. Microbiol., 7(1), 77-81 (1978).
Schaefer, R. L. et al., J. Clin. Microbiol., 10(5), 669-672 (1979).
"Gonochek", E. Y. Laboratories, Inc., 127 North Amphlett Boulevard, San Mateo, Calif.
"Tazolectins", E. Y. Laboratories, Inc., 127 North Amphlett Boulevard, San Mateo, Calif.

Primary Examiner—Sidney Marantz
Attorney, Agent, or Firm—James R. McBride

[57] ABSTRACT

A method for identification of a microorganism includes combining in a suitable fluid the microorganism and a latex containing a particle coated with about 1 to 150 μg per ml of latex of a lectin specific for the microorganism. Binding of the microorganism and lectin causes agglutination which is detected. The microorganism is identified by the agglutination as that organism which is specific for the lectin. The invention includes a reagent which may be included with other materials in a kit of materials useful for performing the method of the invention.

13 Claims, No Drawings

LECTIN-COATED LATEX AGGLUTINATION ASSAY FOR NEISSERIA GONORRHOEAE

BACKGROUND OF THE INVENTION

1. Field of the Invention

This invention relates to the identification of unknown microorganisms. More particularly, it relates to a method and materials for identification of *Neisseria gonorrhoeae* by agglutination subsequent to a specific binding reaction between the microorganism and a limited quantity of a specific lectin coated onto a polymeric particle.

2. Description of the Prior Art

The identification of *Neisseria gonorrhoeae* (N.g.), *Neisseria meningitidis* (N.m.) and other Neisseria (N.) species in the clinical laboratory is usually accomplished by time consuming culture followed by direct fluorescent antibody detection methods or carbohydrate degradation tests. More rapid carbohydrate degradation tests have been devised which reduce the time required for identification after primary culture by eliminating the requirement for growth during the identification test. In these methods, identification of an isolate is usually achieved after 4 to 5 hours of incubation. Carboyhydrate degradation reactions are generally reliable for the identification of Neisseria species, but there are reports of strains of N.g. and N.m. with aberrant carbohydrate reactions.

D'Amato et al. (*J. Clin. Microbiol.* 7, 77, (1978)) described the use of chromogenic substances instead of carbohydrate degradation for identification and differentiation of N.g. and N.m. from each other and from other Neisseria species.

Lectins are proteins or glycoproteins of nonimmune origin having two or more binding sites which recognize and bind to specific sugars or sugar sequences present in the cell membranes of most microorganisms, including N.g. Lectin-based agglutination tests which rely on this binding are useful in diagnostic microbiology and represent a significant improvement over costly and labor-intensive agglutination tests using antibodies.

A lectin-specific slide agglutination test for identification of N.g. was disclosed by Schaeffer et al. (*J. Clin. Microbiol.* 10, 669 (1979) and U.S. Pat. No. 4,389,689) and refined by Doyle et al. (*J. Clin. Microbiol.* 19, 383 (1984)). This method using wheat germ agglutinin (WGA) was further improved by the modification of Yajko et al. (*J. Clin. Microbiol.* 19, 380 (1984)) wherein a lectin was combined with a chromogenic substance.

Slifkin et al. (*J. Clin. Microbiol.* 19, 83 (1984)) used a lectin coupled to polystyrene particles as an agglutination reagent for the detection of Group C streptococcal antigen extracts.

A wide variety of lectin kits is marketed by E. Y. Laboratories, Inc., San Mateo, CA, under the trade names Limb TM, Taxonolectins TM, and Gonochek TM. The Limb TM kits are lectins linked to macrobeads. The GONOCHECK kit is directed specifically to identification of N.g.

Despite the improvements in lectin-based microorganism identification described above, unsolved problems still exist. In particular, agglutination of closely related species by a single lectin may reduce assay specificity and cause erroneous results. It is toward the solution of this problem that the present invention is directed.

SUMMARY OF THE INVENTION

One aspect of the present invention is a method for identification of an unknown microorganism which includes preparing a fluid mixture of the microorganism and an agglutination reagent. The reagent consists of an emulsified solid particle having coated thereon about 1 to 150 ug per ml of emulsion of a lectin specific for a sugar sequence characteristic of a known microorganism wherein the unknown microorganism binds to the lectin. The method includes observing agglutination and identifying the unknown microorganism as the known microorganism by the occurrence of agglutination.

In a preferred embodiment of the invention wherein the method is used to determine whether an unknown microorganism is N.g., the lectin is WGA coated onto a polymeric particle in a latex. The preferred method includes providing conditions conducive to binding the microorganism to the WGA, observing the mixture for agglutination and identifying the microorganism as N.g. if agglutination is observed and concluding that the microorganism is not N.g. if no agglutination occurs. In the most preferred embodiment of the invention, the reagent is a latex containing about 0.7 to 1.5% by weight of the polymeric particle having coated thereon about 10 to 90 ug. of WGA per ml of latex.

Another aspect of the invention includes a reagent for performing the method of the invention consisting of a lectin coated onto an emulsified solid particle. The reagent may be included in a kit of materials useful for performing the method of the invention.

In accordance with the method of the invention, microorganisms are agglutinated and thereby identified by an agglutination reagent having a limited quantity of lectin coated onto a particle in a latex. Agglutination is highly specific whereby closely related species are not agglutinated and erroneous identification is thus avoided.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

In accordance with the method of the invention, an unknown microorganism may be identified by observing agglutination subsequent to a specific binding reaction between a sugar sequence on the microorgnaism and a lectin attached to a solid particle. Any microorganism which binds specifically to a lectin may be identified by the method of the invention. Exemplary of, but not limited to, microorganisms which may be identified and their specific binding lectins are N.g., WGA; Candida albicans, concanavalin A; and coagulase positive Staphylococci, limulin.

The microorganisms to be identified may be from any source, such as soil, water, milk, or, most likely, from a body fluid, such as blood, urine, cerebrospinal fluid, synovial fluid, pleural fluid and the like. Identification may be performed directly in the source fluid, or, preferably, the microorganisms are cultured in a conventional liquid or solid growth medium, and the cultured microorganisms are identified in accordance with the method of the invention.

After culturing, the microorganisms and a specific agglutination reagent, as described below, are combined. A colony or other aliquot of the cultured microorganisms may be introduced into a suitable suspending fluid, as, for example, a buffer or saline at a concentration of about $10^3$ to $10^9$ preferably about $10^6$ colony forming units (cfu) per ml. The agglutination reagent may be added to the microorganism suspension, or alternatively, the reagent may be introduced into the suspending fluid prior to addition of the microorganisms.

The agglutination reagent is an emulsified solid particle coated with a lectin which binds specifically to antigenic sugar sequences on the surface of the microorganism. Any suitable solid particle may be used which can be coated with the lectin and which does not interfere with the binding reaction between the microorganism and the lectin. The preferred solid particle is a polymeric particle such as, for example, a polyolefin, polystyrene or polyacrylate. The polymeric particle may be of any suitable size, preferably from about 0.1 to 5.0 um, most preferably from about 0.5 to 1.2 um in diameter, and preferably are used in the form of a latex.

Coating of the lectin onto the particle may be carried out by any conventional procedure, such as covalent coupling, or, preferably by physical adsorption. The quantity of lectin coated by adsorption is determined by the quantity of lectin in the coating mixture and the conditions used in the coating procedure. In covalent coupling, a reactive functional group on the particle is reacted with a reactive functional group on the lectin. For example, a carboxyl group on the particle and an amino group on the lectin may be covalently bonded by a coupling agent, such as a water soluble carbodiimide, to form an amide group. In covalent coupling, the quantity of lectin coated is determined by reagent concentrations in the coupling reaction mixture. In the present invention, the quantity of lectin coated onto the particle is given in micrograms of lectin per ml of a specific weight percentage composition of latex.

After the desired amount of specific lectin is coated onto the particle, the remaining binding sites on the particle may be filled by an inert protein. The inert protein may be any protein as, for example, ovalbumin, which can be attached to the particle and which does not react with the microorganism or interfere in any way with the specific binding reaction between the microorganism and the lectin. Methods to prepare polymeric particles and methods for covalent and adsorptive coating of lectins and inert proteins to polymeric particles are well known and no further details in this regard are considered to be necessary for a complete understanding of the invention.

The choice of agglutination reagent to be used depends on the suspected identification of the unknown microorganisms. For example, if the microorganism is suspected to be N.g., the lectin coated on the solid particle preferably is WGA. On the other hand, if the microorganism is suspected to be *Candida albicans* or coagulase positive Staphylococci, the lectin preferably is concanavalin A or limulin respectively.

It has been found that the quantity of lectin coated onto the particle and the concentration of the particle in the fluid suspension are relevant in determining the specificity of the agglutination reagent. If the reagent contains too much coated lectin, or the particle concentration in the latex is too high, the specificity of the reagent decreases and undesirable binding of different, but closely related, microorganisms may occur, leading to agglutination and erroneous identification. On the other hand, the reagent shall contain sufficient lectin to bind and thereby agglutinate the unknown microorganism. In accordance with the method of the invention, the reagent may contain about 1 to about 150 ug of lectin per ml of latex, and the concentration of the particle in the latex may be about 0.1 to 5.0 weight percent. In the most preferred embodiment of the invention wherein the unknown microorganism is suspected to be N.g., the quantity of WGA coated onto the particle may be from about 10 to 90 ug per ml, and the particle concentration in the latex may be about 0.7 to 1.5 weight percent.

The quantity of agglutination reagent to be added depends on the concentration of unknown microorganisms in the suspension. In general about equal volumes of the reagent and the microorganism suspension are combined when the suspension of microorganisms contains about the preferred $10^6$ organisms per ml. If the concentration of microorganisms differs substantially from this preferred value, the quantity of the reagent may be increased or decreased accordingly.

After combining the agglutination reagent and the microorganisms in the suspending fluid, thorough mixing of the two components by any suitable technique is carried out, and the mixture is subjected to conditions conducive to binding and agglutination. If desired or necessary, incubation may be carried out at any suitable temperature and for any suitable time, preferably for about 1 minute to 1 hour at 20°–40° C.

The mixture is observed for about 1 minute to 1 hour, preferably about 2 to 10 minutes for agglutination. Any suitable observation means, as for example, microscopic, or preferably, visual may be used. The presence of agglutination establishes the identity of the unknown microorganism in accordance with the specific lectin employed. Thus, an unknown microorganism is identified as N.g. if agglutination is observed when the particle is coated with WGA. If agglutination does not take place with WGA coated particles, the microorganism is not N.g. Positive identification of the organism may then be obtained by repeating the method of the invention using other lectin-particle agglutinating reagents known to be specific for a given microorganism.

The invention includes an agglutination reagent consisting of an emulsified solid particle coated with from 1 to 150 ug per ml of emulsion of lectin specific to a known microorganism. The reagent may be combined in a kit of materials including other reagents and solutions, exemplified by buffers, saline and the like useful in identifying a microorganism in accordance with the method of the invention. There may also be present in the kit a negative control consisting of an emulsion containing a solid particle which does not have any coated lectin. The reagents and solutions may be supplied in the kit in individual packages or receptacles, or one or more reagents or solutions may be combined in a single receptacle. Additional implements, such as receptacles, stirrers, slides and the like may also be supplied for the convenience of the technician.

The following examples are provided to further describe the invention, but are not to be construed in any way as limitative of the invention.

EXAMPLE I

General Procedure For Lectin Coating By Covalent Coupling

Four milliliters of a 2.5% suspension of latex beads having free carboxyl groups (Polysciences #7759) were washed by suspension, centrifugation, and decantation using 5 ml of 0.02M potassium phosphate buffer, pH 4.4 (PPB), and suspended in 5 ml of PPB. A 2% solution of 1-ethyl-3-(3-dimethylaminopropyl) carbodiimide (EDC) in PPB (5 ml) was added dropwise to the bead suspension and the mixture was set aside for 3.5 hours at room temperature. The EDC-activated beads were washed twice with 5 ml of 0.15M NaCl and resuspended in 5 ml of a buffer consisting of 0.01M Tris and 0.15M NaCl (TBS). WGA, 1.5 mg in 5 ml TBS was added dropwise to the suspension followed by 5 ml TBS, and the mixture was stirred at room temperature for 16 hr. The WGA-derivatized beads were washed once with 5 ml TBS, suspended in 10 ml of TBS containing 1 mM 2-aminoethanol, stirred for 8 hr at room temperature, and centrifuged. The pelleted beads were resuspended in 10 ml 0.2% ovalbumin in TBS, stirred for 38 hr. at room temperature, washed twice in 10 ml of a solution consisting of 0.02M glycine, 0.034M NaCl, 0.05% Tween-20 and 0.02% sodium azide adjusted to pH 8.2 with NaOH (GBST), and resuspended in 4.0 ml GBST containing 0.2% ovalbumin. A 2.5% bead suspension containing 150 ug WGA per ml was thereby obtained.

EXAMPLE II

General Procedure For Agglutination

Microorganisms were suspended at the desired concentration in a solution containing 0.05M sodium phosphate and 0.2M NaCl chloride adjusted to pH 7.2 with sodium hydroxide (PBS). Equal volumes of the latex suspension and microorganism suspension were combined and the mixture was gently rotated and observed for agglutination every 2 minutes for 10 minutes.

EXAMPLE III

The coupling procedure of Example I was used to prepare latex beads having 60, 30, 15, 8, 6, 2 and 1 ug/ml of WGA coated on beads in 1% suspensions by appropriate modification of the concentration of WGA in the TBS solution added to the EDC-activated beads. The agglutination procedure of Example II was applied to the microorganisms listed in Table I. In addition, the microorganisms were tested for agglutination with a negative control which consisted of underivatized latex. Agglutination was essentially the same with beads having WGA concentrations of 30, 15, and 8 ug/ml of 1% bead suspension. At lower WGA concentrations, sensitivity to N.g. was lost. The results are shown in Table I with the degrees of agglutination designated by the following code.

0-fine agglutinates
1-agglutination just visible to naked eye
2-small, easily-seen agglutinates
3-medium-sized clumps, clear supernatant
4-very few clumps in clear supernatant

TABLE I

| Organism | Control Latex | Test Latex |
| --- | --- | --- |
| M2255 N. gonorrhoeae | N.I.* | 2-3+ |
| M2242 N. gonorrhoeae | N.I. | 2+ |
| M1842 N. gonorrhoeae | Trace | 2+ |
| M2046 N. gonorrhoeae | 1+ | 2+ |
| M2065 N. gonorrhoeae | Trace | 1-2+ |
| M2010 N. gonorrhoeae | N.I. | 2-3+ |
| M1980 N. gonorrhoeae | N.I. | 2+ |
| M2030 N. gonorrhoeae | 1+ | 2-3+ |
| M2026 N. gonorrhoeae | 0 | 1+ |
| GB703 N. subflava | 0-1+ | 1+ |
| MFO N. flavescens | 2-3+ | 3-4+ |
| GB41-1 N. sicca | 1-2+ | 2+ |
| 1229 N. sicca | 0 | 0 |
| M2386 N. meningitidis | 0 | 1-2+ |
| M2401 N. meningitidis | 0-1+ | 1+ |
| M2349 N. meningitidis | 0 | 0 |
| **M4077 B. catarrhalis | 0-trace | 0-trace |
| M2343 B. catarrhalis | 2+ | 2+ |
| JH4-1 B. catarrhalis | 1-2+ | 2+ |

*not interpretable
**Branhamella catarrhalis

EXAMPLE IV

General Procedure For Lectin Coating By Physical Adsorption

Two milliliters of a 10% suspension of 0.868 um "Physisorb" latex beads (lot #1A44, Dow) were washed three times by suspension of the beads in 20 ml of a solution of 0.02M glycine, 0.034M NaCl, 0.02% $NaN_3$ adjusted to pH 8.2 with NaOH (Gly-NaOH buffer) followed by centrifugation and decantation. The beads were then suspended in 2.0 ml of Gly-NaOH buffer and divided into two equal portions. Test beads were prepared by adding 1.0 ml of a solution of 650 ug/ml WGA in Gly-NaOH buffer to a 1.0 ml portion of the bead suspension. Control beads were prepared by adding 1.0 ml of 0.07% ovalbumin in Gly-NaOH buffer to 1.0 ml of bead suspension. Both suspensions were gently shaken at 37° C. for 75 min., centrifuged, and the pelleted beads in each tube were suspended in 1.0 ml of a solution of 0.2% ovalbumin in Gly-NaOH buffer. After incubation with shaking at 37° C. for 15 min, the suspensions were centrifuged, and the sensitized beads were washed three times by centrifugation with Gly-NaOH buffer containing 0.05% Tween 20, and three times with PBS. Finally both samples of latex beads were suspended in 10 ml PBS, pH 7.5 and contained 65 ug/ml of 1% bead suspension.

EXAMPLE V

The microorganisms listed in Table II were suspended at a concentration of about $10^6$ fu per ml in PBS, pH 7.5, and the procedure of Example II was followed.

Agglutination results are shown in the Table II. It is seen that only N.g. agglutinated strongly with the lectinized beads while showing little or no agglutination of the control latex. Other organisms are differentiated by the absence of any agglutination with test or control by equal agglutination of test and control.

TABLE II

| ORGANISM | MIN | TEST | CONTROL |
| --- | --- | --- | --- |
| N. gonorrhoeae #111 | 4 | +2 | 0 |
|  | 10 | +2 | 0 |
| N. gonorrhoeae #115 | 4 | +2 | 0 |
|  | 10 | +2 | 0 |
| N. gonorrhoeae #116 | 4 | +2 | 0 |
|  | 10 | +2 | 0 |
| N. gonorrhoeae #JL | 4 | +2 | +1 |
|  | 10 | +2 | +1 |

TABLE II-continued

| ORGANISM | MIN | TEST | CONTROL |
|---|---|---|---|
| N. meningitidis #171 | 4 | 0 | 0 |
| | 10 | 0 | 0 |
| N. meningitidis #68702 | 4 | 0 | 0 |
| | 10 | +1 | 0 |
| N. meningitidis #55592 | 4 | 0 | 0 |
| | 10 | 0 | 0 |
| N. sicca #4-1-4 | 4 | 0 | 0 |
| | 10 | +1 | 0 |
| N. sicca #4-5-4 | 4 | 0 | 0 |
| | 10 | 0 | 0 |
| N. lactamica #23970 | 4 | 0 | 0 |
| | 10 | +1 | +1 |
| B. catarrhalis #M1102 | 4 | +1 | +1 |
| | 10 | +1 | +1 |
| Moraxella species | 4 | +1 | 0 |
| | 10 | +1 | +1 |

Thus, the invention provides a method and materials whereby an unknown microorganism including N.g., may be identified by an agglutination reaction employing a specific lectin coated onto a polymeric particle. The quantity of lectin coated onto the particle and the concentration of the particle in the latex is limited so that non-specific binding between the lectin and other closely related microorganisms is avoided. Agglutination with the related microorganisms is thereby prevented and the unknown microorganism may be identified accurately.

What is claimed is:

1. A method for determining whether an unknown microorganism is *Neisseria gonorrhoeae* comprising:
   (a) preparing a mixture in a fluid by combining an unknown microorganism suspected to be *Neisseria gonorrhoeae* and a reagent consisting of a latex containing from about 0.1 to 5.0 weight percent of a polymeric particle, said particle having coated thereon from about 1 to 150 ug per ml of latex of wheat germ agglutinin, said coating of said wheat germ agglutinin onto said particle being effected by physical adsorption;
   (b) subjecting said mixture to conditions conducive to binding said microorganism to said wheat germ agglutinin;
   (c) observing said mixture for agglutination; and
   (d) identifying said microorganism as *Neisseria gonorrhoeae* if agglutination is observed and determining that said microorganism is not *Neisseria gonorrhoeae* if agglutination is not observed.

2. The method in accordance with claim 1 wherein said fluid is selected from the group of fluids consisting of a buffer or saline.

3. The method in accordance with claim 1 wherein said polymeric particles are selected from the group of particles consisting of polyolefins, polyacrylates, and polystyrenes.

4. The method in accordance with claim 1 wherein said agglutination is observed visually.

5. The method in accordance with claim 1 wherein said agglutination is observed microscopically.

6. A method for determining if an unknown microorganism is *Neisseria gonorrhoeae* comprising:
   (a) preparing a mixture in a fluid by combining a suspension of an unknown microorganism suspected to be *Neisseria gonorrhoeae* with a reagent consisting of a latex containing from about 0.7 to 1.5 weight percent of a polymeric particle having coated thereon from about 10 to 90 ug per ml of latex of wheat germ agglutinin, said coating of said wheat germ agglutinin onto said particle being effected by physical adsorption, and a quantity of an inert protein sufficient to fill essentially all of the binding sites of said particle left unfilled by said wheat germ agglutinin;
   (b) subjecting said mixture to conditions conducive to binding of said microorganism to said wheat germ agglutinin;
   (c) observing said mixture for agglutination; and
   (d) identifying said microorganism as *Neisseria gonorrhoeae* if agglutination is observed and determining that said microorganism is not *Neisseria gonorrhoeae* if agglutination is not observed.

7. The method in accordance with claim 6 wherein said inert protein is ovalbumin.

8. A kit of materials for identifying *Neisseria gonorrhoeae* comprising a reagent consisting of a latex containing about 0.1 to 5.0 weight percent of a solid particle having coated thereon by physical adsorption from about 1 to 150 ug per ml of latex of wheat germ agglutinin and an additional reagent selected from the group of reagents consisting of saline and a buffer.

9. The kit in accordance with claim 8 further comprising a negative control consisting of a latex containing from about 0.1 to 5.0 weight percent of said solid particle wherein said particle is free of a lectin coating.

10. The kit in accordance with claim 8 further comprising one or more implements useful in performing said identification.

11. The kit in accordance with claim 10 wherein said implement is a receptacle.

12. The kit in accordance with claim 10 wherein said implement is a stirrer.

13. The kit in accordance with claim 10 wherein said implement is a slide for observing said agglutination.

* * * * *